(12) United States Patent
Seitlinger et al.

(10) Patent No.: US 9,974,550 B2
(45) Date of Patent: May 22, 2018

(54) TIBIAL CUTTING BLOCK

(71) Applicant: Arthrex, Inc., Naples, FL (US)

(72) Inventors: Gerd Seitlinger, Oberalm (AT); Florian Dirisamer, Linz (AT); Uta Moll, Feldkirchen (DE); Stéphane Naudin, Krailling (DE); Frank Uhing, Munich (DE); Michel Gerlinde, Munich (DE)

(73) Assignee: ARTHREX, INC., Naples, FL (US)

( * ) Notice: Subject to any disclaimer, the term of this patent is extended or adjusted under 35 U.S.C. 154(b) by 296 days.

(21) Appl. No.: 14/833,821

(22) Filed: Aug. 24, 2015

(65) Prior Publication Data

US 2016/0051268 A1 Feb. 25, 2016

(30) Foreign Application Priority Data

Aug. 25, 2014 (EP) .................................... 14182137

(51) Int. Cl.
*A61B 17/17* (2006.01)
*A61B 17/15* (2006.01)
*A61B 17/88* (2006.01)
*A61B 17/86* (2006.01)
*A61B 17/92* (2006.01)

(52) U.S. Cl.
CPC ........ *A61B 17/1764* (2013.01); *A61B 17/157* (2013.01); *A61B 17/864* (2013.01); *A61B 17/8886* (2013.01); *A61B 17/92* (2013.01)

(58) Field of Classification Search
CPC ... A61B 17/864; A61B 17/8886; A61B 17/92; A61B 17/157; A61B 17/1764
See application file for complete search history.

(56) References Cited

U.S. PATENT DOCUMENTS

| 5,129,909 A | * | 7/1992 | Sutherland | ........... A61B 17/155 606/53 |
| 2010/0168753 A1 | * | 7/2010 | Edwards | .............. A61B 17/155 606/88 |
| 2012/0109135 A1 | * | 5/2012 | Bailey | .................... A61B 17/15 606/87 |

* cited by examiner

*Primary Examiner* — Christian Sevilla
(74) *Attorney, Agent, or Firm* — Carlson, Gaskey & Olds, P.C.

(57) ABSTRACT

A tibia cutting block for performing precise cuts into a tibia comprises an approximately cuboid body with a tibia attachment side and opposing thereto a front side. The body has a cutting guide slot extending from a top side into the body, a blade holding slot extending from a right side or a left side into the body, a first anchoring pin hole which is close to the intersection of a first plane defined by the blade holding slot and a second plane defined by the a cutting guide slot, a second anchoring pin hole distant from the first anchoring pin hole and a reference pin guide. All are penetrating the body from the front side to the tibia attachment side.

10 Claims, 11 Drawing Sheets

TIBIAL CUTTING BLOCK

BACKGROUND OF THE INVENTION

Field of the Invention

The invention relates to surgical devices, and more particularly to orthopedic devices for performing knee arthroplasty.

Description of the Related Art

Specific tools and instruments are required for knee arthroplasty, and specifically for the treatment of localized unicondylar cartilage degeneration as a result of osteoarthritis or post-traumatic arthrosis in the medial or lateral compartment of the knee. A critical step in this kind of surgery is the preparation of bones to adapt for tibial resurfacing implants. As the precise location of these implants is essential for a good mechanical function and a long lifetime of the implant, the cuts into the bone material must be performed with high precision.

A device for preparing a proximal tibia for a tibial implant is disclosed in US 2013/0116698 A1. The device provides a main body and a reference bench coupled thereto. Other devices or instruments may be coupled to the reference bench to perform sectional cuts into the bone.

In WO 2013/063418 A2, an instrument for gauging the size, position, and/or rotational orientation of one or more receptions of a proximal tibia for receipt of a tibial implant is disclosed. It comprises a cutting guide with a mounting base, a tibia gauge, and a reference plate to place the cutting guide at a precise location with respect to the tibia.

Another instrument set for preparing a proximal tibia is disclosed in US 2012/0316563 A1. This instrument set comprises a tibial resection block to be fixed to an anterior portion of the proximal tibia. It furthermore has a vertical cut guide having a body, a medial arm, a lateral arm, and a locking arm. The arms provide for a placement of the tibial resection block at a predetermined position of the tibia.

All these instruments or instrument sets have in common that they are comparatively complex. They comprise of several complex shaped parts which are difficult to use, as they allow multiple adjustments to find the correct position for a cut at the tibia. Generally, each setting or adjustment bears the potential risk of a failure. Furthermore, complex tools generally are expensive and bear higher maintenance costs compared to simple instruments and tools.

SUMMARY OF THE INVENTION

The problem to be solved by the invention is to provide a tool for performing precise cuts into the tibia. The tool should be usable for minimal invasive surgery, it should have a simple structure, a small size, and it should require only a minimal number of settings and/or adjustments when performing a surgery.

Solutions of the problem are described in the independent claims. The dependent claims relate to further improvements of the invention.

A tibia cutting block has a body with a tibia attachment side, which is essentially a planar surface for contacting the tibia. Preferably, the body is approximately cuboid shaped. It may have rounded edges. Opposed to the tibia attachment side is a front side.

The cutting block has a first anchoring pin hole and a second anchoring pin hole for inserting anchoring pins through the cutting block into the tibia. The cutting block can be held in a defined position at the tibia by these anchoring pins. Both anchoring pin holes are anterior-posterior oriented and preferably penetrate the body from the front side to the tibia attachment side. These anchoring pin holes define channels through the cutting block, whereas the channels preferably are distant from each other and preferably are under an angle which most preferably is in a range between 10 to 30 degrees. This results in the holding pins penetrating into the tibia under the same angle of the channels, which not only allows to hold the cutting block in a plane parallel to the tibia attachment side, but also prevents the cutting block from moving away from the tibia.

The cutting block furthermore has a reference pin guide for guiding a reference pin. This reference pin guide may be an anterior-posterior oriented groove preferably extending from the front side to the tibia attachment side. In an alternative embodiment, it may be a hole through the body. To hold the reference pin within the reference pin guide, a reference pin lock may be provided. This lock may be pivotable, tiltable or rotatable about a lock axis and it may be held in a locked position by a lock arrester. Preferably, the reference pin lock locks the reference pin to the cutting block only allowing the cutting block to slide along a longitudinal axis of the reference pin and/or to rotate about said axis.

A cutting guide slot extends through the body from a top side in superior-inferior direction and penetrates the body from the front side to the tibia attachment side in anterior-posterior direction. This cutting guide slot is for guiding a saw blade or knife for making a first cut into the bone.

A blade holding slot extends through the body in anterior-posterior direction from the front side to the tibia attachment side and has a length in left-right direction. The terms left and right relate to a patient's view. The blade holding slot is for holding a reference blade and therefore preferably has a width slightly larger than the thickness of a reference blade. Therefore, the blade holding slot preferably has a width smaller than the diameter of an anchoring pin hole. This may further prevent erroneously inserting an anchoring pin into the blade holding slot, as the anchoring pin preferably has a larger diameter than the width of the blade holding slot. Preferably, the cutting guide slot and the blade holding slot are under a right angle. Preferably, they do not intersect.

In a preferred embodiment, the first anchoring pin hole is close to or most preferably at the intersection of the planes defined by the cutting guide slot and the blade holding slot. Preferably, the first anchoring pin hole is not connected to at least one of the cutting guide slot and the blade holding slot to increase mechanical stability of the cutting guide block.

For holding the cutting block, a connector may be provided by which a grip or any other device may be attached. The connector is preferably attached by methods like welding or screwing to the cutting block, most preferably to the bottom side of the cutting block.

Dependent on which section of the tibia has to be cut and dependent on whether the left or the right tibia has to be treated, the tibia cutting block may have reversed left and right sides, whereas for example the first anchoring pin hole and the cutting guide slot would be at the right side, while the second anchoring pin hole is at the left side.

A further embodiment relates to a total prosthesis cutting block. This cutting block may be used for a total tibia cut. It is similar to the cutting block described above. The main difference is, that it has no cutting guide slot for a superior-inferior cut but a second side with a second blade holding slot, basically in the same plane as the first blade holding slot. It is further preferred to have a third anchoring pin hole at the side of the second blade holding slot. The second blade holding slot may be used as an alternate to the first blade holding slot for holding a reference blade. It may also be used as a cutting guide for a cutting blade in left-right or right-left direction.

A reference pin has an elongated shaft and preferably hook-shaped tip at its end. The shaft has a side to fit into the reference pin guide groove of the cutting block. Preferably, the reference pin has a cylindrical shaft. It is further preferred, if the reference pin has a scale for measuring/indicating the position of the reference pin with respect to the cutting block. This may be used to measure the depth of the tibial plateau. It is further preferred if the reference pin has a connector at the end opposite to the hook-shaped tip. This allows a handle or any fixation device to attach to the reference pin for improving handling.

The tibia cutting block may be made of any suitable material, like plastic or metal. Preferably, it is made of a surgical grade steel. Preferably, it is a single piece of metal having at least two anchoring pin holes, a cutting guide slot and a blade holding slot.

A method of tibia preparation comprises a first step of inserting a reference pin with a hook-shaped tip in an anterior-posterior direction between the tibia and the femur. For simplifying insertion of the hook-shaped tip, it may be rotated into a lateral direction. When the hook-shaped tip has passed the posterior side of the tibia, it may be adjusted so that the hook-shaped tip is oriented towards the tibia. Then, the reference pin may slowly be pulled back until the hook-shaped tip contacts the tibia. In a next step, the cutting block may be attached to the reference pin, preferably by inserting the reference pin into a reference pin guide of the cutting block, which most preferably is a groove. This reference pin guide of the cutting block preferably is in an anterior-posterior direction. After inserting the reference pin, it may be locked by a reference pin lock, which preferably is a slider pivotably about an axis and which further may be held in its locked position by a lock arrester. Preferably, after locking the reference pin, the cutting block can only be moved along the center axis of the reference pin and/or be pivoted about this center axis. Preferably, all other movements are blocked. Preferably, the step of attaching and/or locking the cutting block to the reference pin is done after the reference pin has been inserted into the knee. It is also possible to attach the cutting block to the reference pin before inserting or during inserting.

The reference pin is preferably aligned between the femoral condyle and tibia plateau/meniscii with its hook-shaped tip located at the posterior tibia. While holding the reference pin in place, the cutting block may be pushed to the anterior tibia. By the reference pin's alignment with the tibia, the position of the cutting block may be defined with respect to the tibia. Preferably, there remains only one degree of freedom, the rotation of the cutting block around the center axis of the reference pin. To define the correct angle, of rotation, a varus-valgus angle setting device may be used. This device preferably comprises of a rod which can be aligned in relation to the tibia. It is preferably connected by an angle adapter to the cutting block. The angle adapter may allow an adjustment of the angle between the rod and the cutting block. Preferably, it has an angle offset indicating scale to indicate the angle adjustment or offset. It is preferred, if the angle adapter is connected to the cutting block by the first anchoring pin hole and/or the blade holding slot. For precise alignment, the angle adapter may have a pin which fits into the first anchoring pin hole. It furthermore may have a straight section, which may be aligned with the blade holding slot. This allows precise guidance of the cutting block by the angle adapter. After this second step, two anatomical landmarks, axis or planes are referenced to the cutting block.

In the following steps, the cutting block is fixed to the tibia. These steps of fixing may be changed in their sequence. A reference blade having at least one spike, preferably two or three spikes, may be inserted through the blade holding slot of the cutting block. The reference blade defines a plane and therefore, any equivalent means for defining a plane may be used. Such equivalent means may be a pair of connected pins. When the at least one, preferably two or more spikes of the reference blade have penetrated into the tibia, the cutting block is firmly held in the tibia in a plane as defined by the blade. After the blade has been inserted, the reference pin and/or the angle adapter and/or the varus-valgus angle setting device may be removed. Removing of the reference pin and the angle adapter may be done at the same time or in any sequence. Then, it is preferred to start with inserting a first anchoring pin through the first anchoring pin hole into the bone. At a later time, a second anchoring pin may be inserted through the second anchoring pin hole into the bone. If a third anchoring pin hole is provided in the cutting block, a third anchoring pin may be inserted therein. It may be sufficient to insert only two anchoring pins in their respective holes. Generally, any sequence of inserting anchoring pins may be chosen.

The tibia resection is described in the following steps. In a first step, a superior-inferior cut may be performed by cutting with a blade guided by the cutting guide slot in the cutting block. Before the next cut, preferably the second anchoring pin through the second anchoring pin hole is removed and the cutting block is also removed. Now, the reference blade together with the first anchoring pin remain in the tibia. Then, a cut parallel to the reference blade may be made in a left-right or right-left direction. This cut is limited by the first anchoring pin. In an alternative method, after at least one, preferably two or more anchoring pins have been inserted, as described above, the reference blade may be removed. A first superior-inferior cut may be performed as described above. Then a cut may be made in a left-right or right-left direction through the blade holding slot. After the second cut, the section which was cut out of the tibia by the previous two cuts can be removed. Later, an implant may be inserted into the cutout of the tibia.

BRIEF DESCRIPTION OF DRAWINGS

In the following the invention will be described by way of example, without limitation of the general inventive concept, on examples of embodiment with reference to the drawings.

DETAILED DESCRIPTION OF THE PREFERRED EMBODIMENTS

Figure 1:
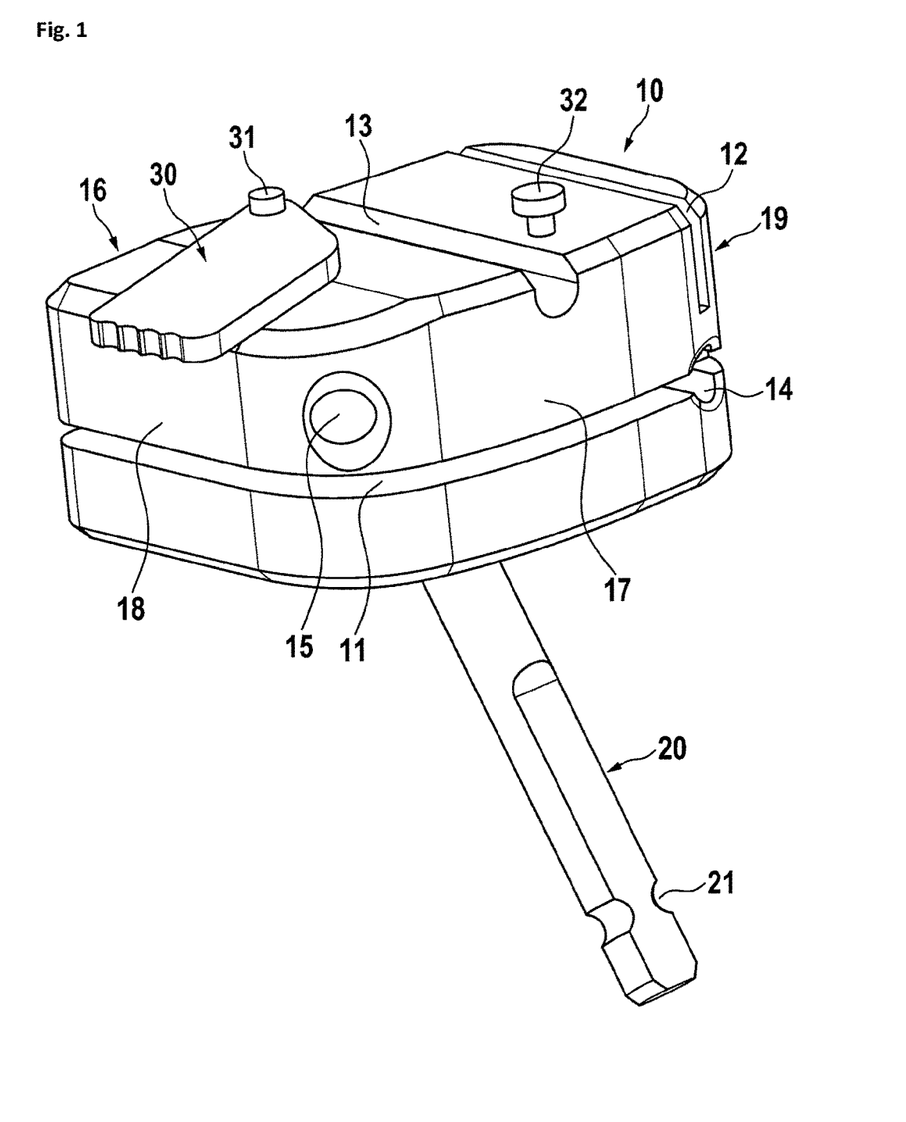
FIG. 1 shows a preferred embodiment of a tibia cutting block.

In FIG. 1, a preferred embodiment of a tibia cutting block is shown. The tibia cutting block 10 has a tibia attachment side 16 and opposed thereto a front side 17. Furthermore, there is a left side 19 and a right side 18. In this embodiment, the right side is oriented to the cruciate ligament while the left side is oriented medial or lateral. Therefore, this cutting block may be used lateral at the right tibia or medial at the left tibia. A cutting block for use lateral at the left tibia or medial at the right tibia, the sides left and right as related to the cutting block are reversed. On the front side, the cutting block has a first anchoring pin hole 14 and a second anchoring pin hole 15, both define basically anterior-posterior oriented channels through the cutting block and allow the insertion of anchoring pins for holding the cutting block to the tibia. Preferably, the channels through the anchoring pin holes are under an angle between 10 and 30 degrees, most preferably between 15 and 25 degrees to prevent the cutting block from being pulled off the tibia. On its top, the cutting block preferably has a reference pin guide 13 for guiding and holding a reference pin (the pin is not shown in this figure). This reference pin guide 13 may be an anterior-posterior oriented groove. The reference pin may be locked by a reference pin lock 30 which may be a lever or slider, or any other means for holding the reference pin within the reference pin guide. The reference pin lock 30 may be pivotable, tiltable or rotatable about a lock axis 31, and it may be held in its closed or locked position by a lock arrester 32. A cutting guide slot 12 extends through the body in anterior-posterior direction and has a length in superior-inferior direction. In this embodiment, the cutting guide slot is at the left side of the cutting block. Preferably, it is above the first anchoring pin hole 14. A blade holding slot 11, which may also be used for guiding a cutting blade, extends through the body in anterior-posterior direction and has a length in left-right direction. Preferably, the first anchoring pin hole 14 is in the same plane as the blade holding slot, or a little bit above this plane, preferably about the thickness of a reference blade (which is not shown in this figure) above the plane of the blade holding slot. Preferably at the bottom side, there may be a connector 20 for connecting a handle or other means for holding or fixing the cutting block. Preferably, the connector has a locking groove 21 for locking an external device to the connector.

Dependent on which section of the tibia has to be cut and dependent on whether the left or the right tibia has to be treated, the tibia cutting block may look like disclosed in this figure. It may also have reversed left and right sides, whereas for example the first anchoring pin hole 14 and the cutting guide slot 12 would be at the right side, while the second anchoring pin hole 15 is at the left side.

Figure 2:
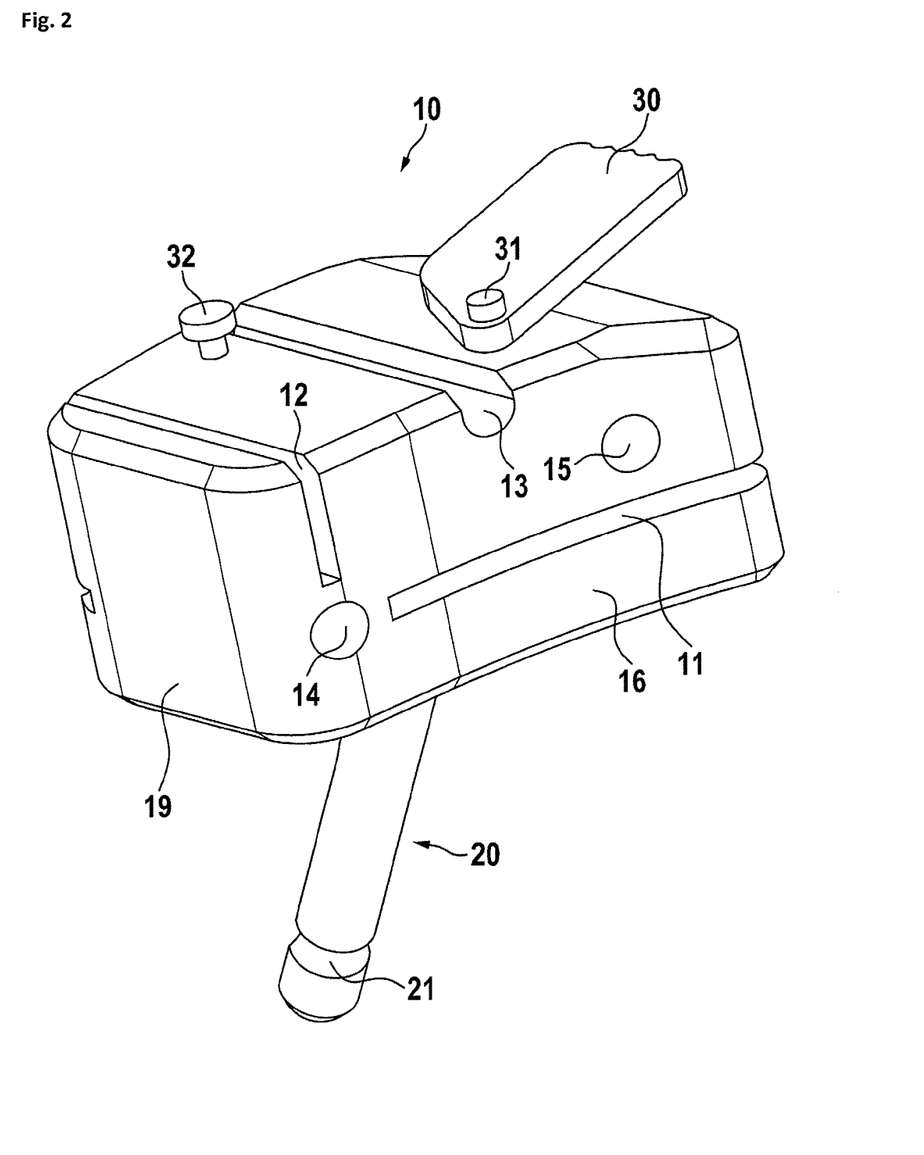
FIG. 2 shows a cutting block from the tibia attachment side.

In FIG. 2, the cutting block of the previous figure is shown from the tibia attachment side 16. Here it can be seen, that the first anchoring pin hole 14 is approximately in the intersection of the plane of the cutting guide slot 12 and the plane of the blade holding slot 11. To maintain mechanical stability of the cutting block, the cutting guide slot 12 and the blade holding slot 11 preferably are not connected to the first anchoring pin hole 14.

Figure 3:
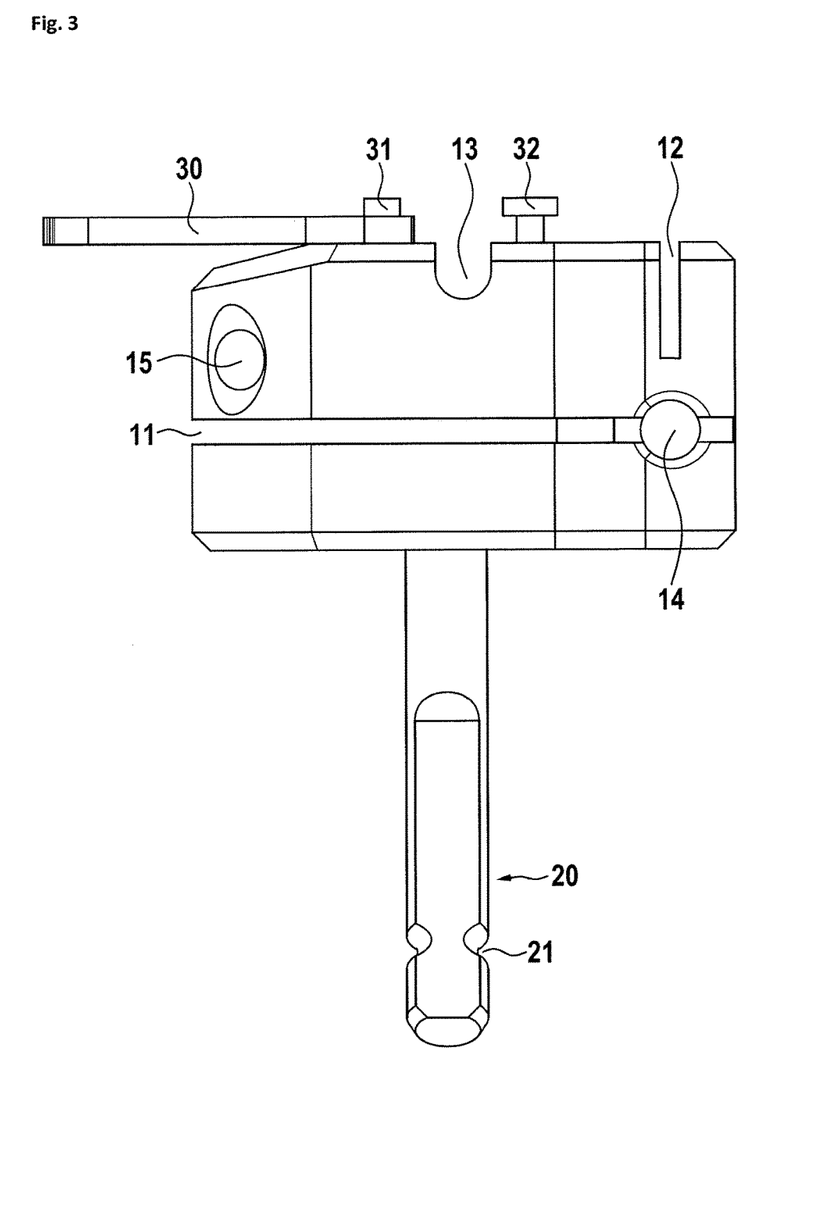
FIG. 3 shows a front side view of the cutting block.

In FIG. 3, a front side view of the cutting block is shown.

Figure 4:
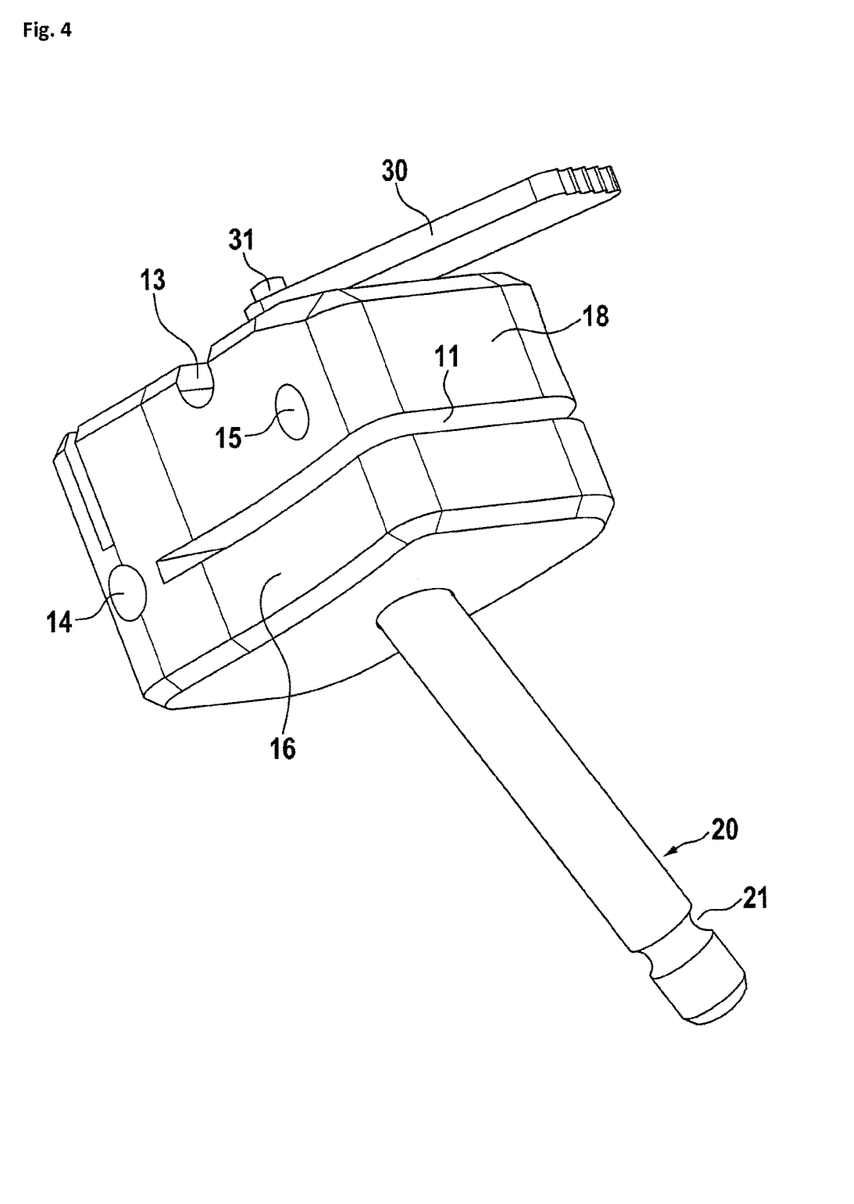
FIG. 4 shows a perspective view of the cutting block.

In FIG. 4, a perspective view of the cutting block is shown.

Figure 5:
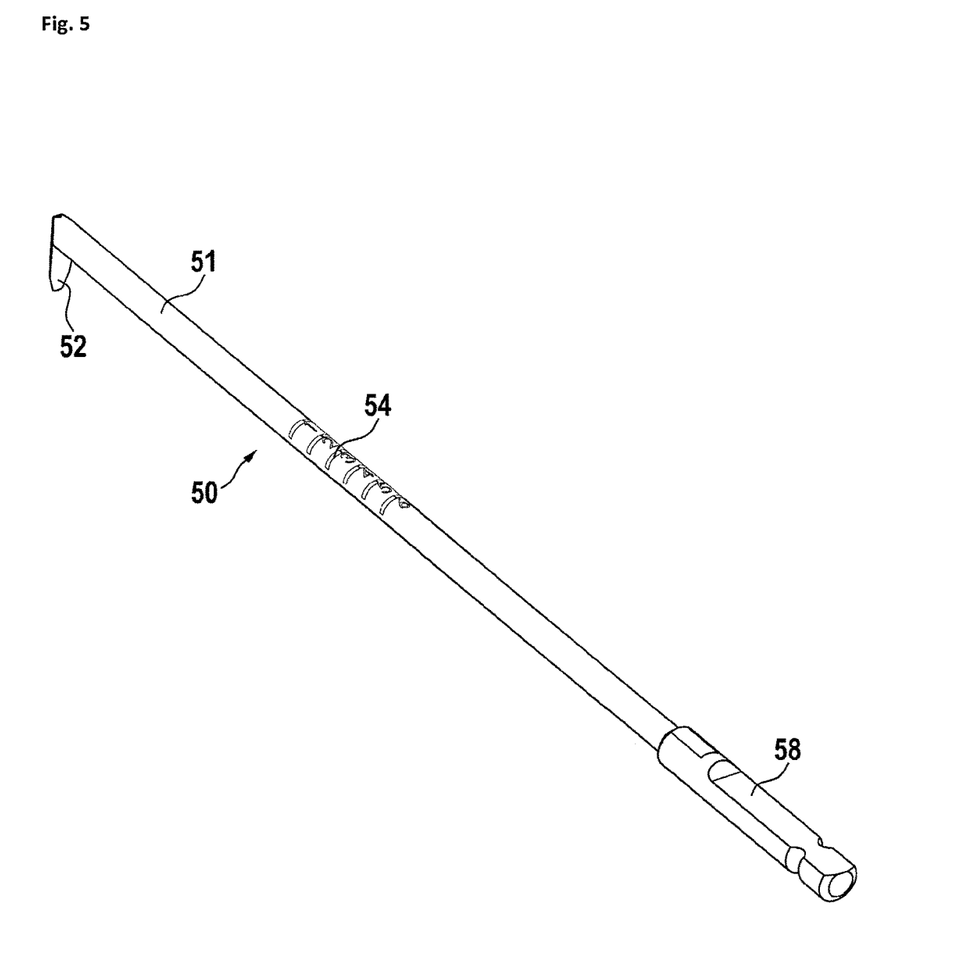
FIG. 5 shows a reference pin.

In FIG. 5, a reference pin 50 is shown. The reference pin has an elongated shaft 51 defining a longitudinal axis and a preferably hook-shaped tip 52 at its end. Preferably, the reference pin has a cylindrical shaft, although the shaft may have any other shape, like a rectangular or elliptical cross-section. For measuring or indicating the position of the reference pin and/or of the hook-shaped tip 52, a scale 54 may be provided. The reference pin may be connected to a handle by means of connector 58.

Figure 6:
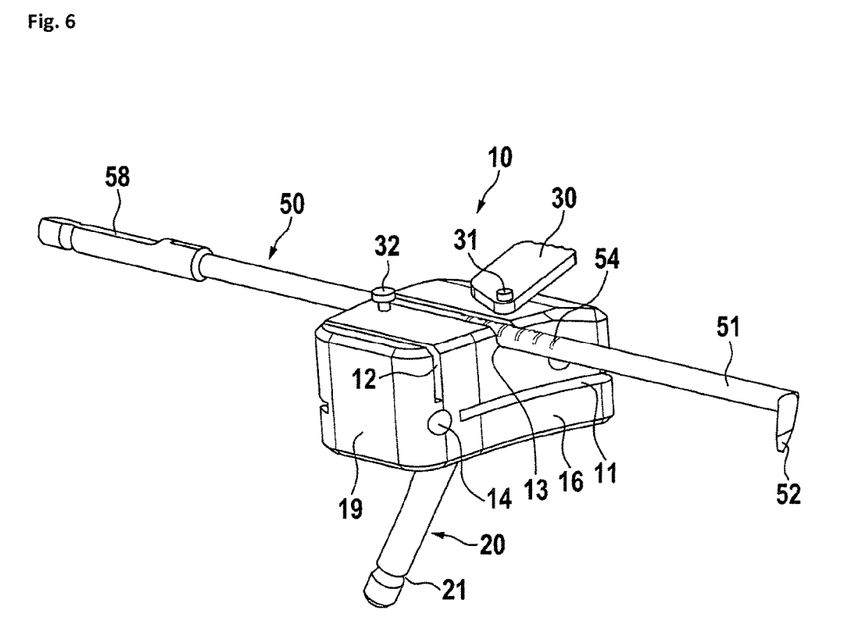
FIG. 6 shows a reference pin within a cutting block.

In FIG. 6, a reference pin is shown when held in a cutting block.

Figure 7:
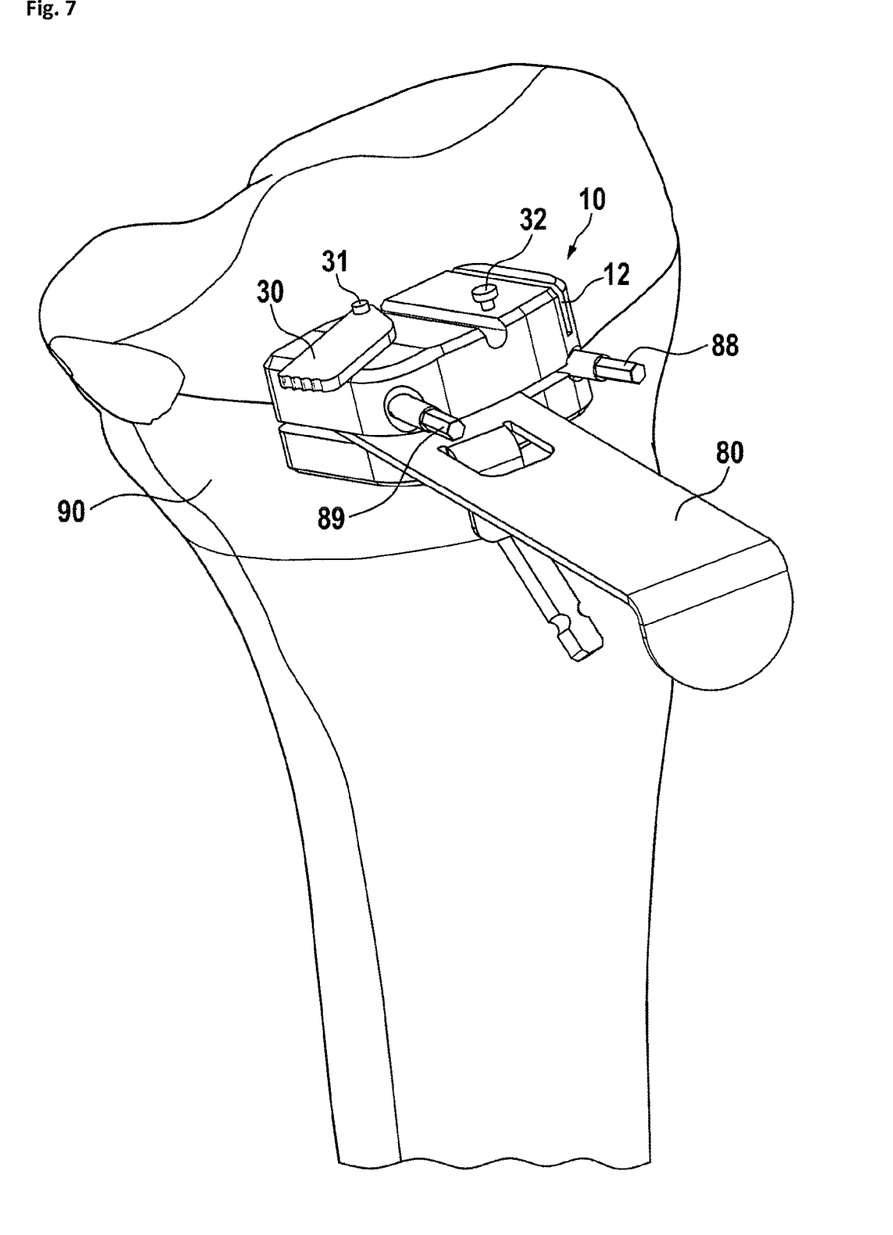
FIG. 7 shows a cutting block attached to a tibia.

In FIG. 7, a cutting block 10 is shown when attached to a tibia 90. The cutting block 10 is held by a first anchoring pin 88, a second anchoring pin 89 and a reference blade 80.

Figure 8:
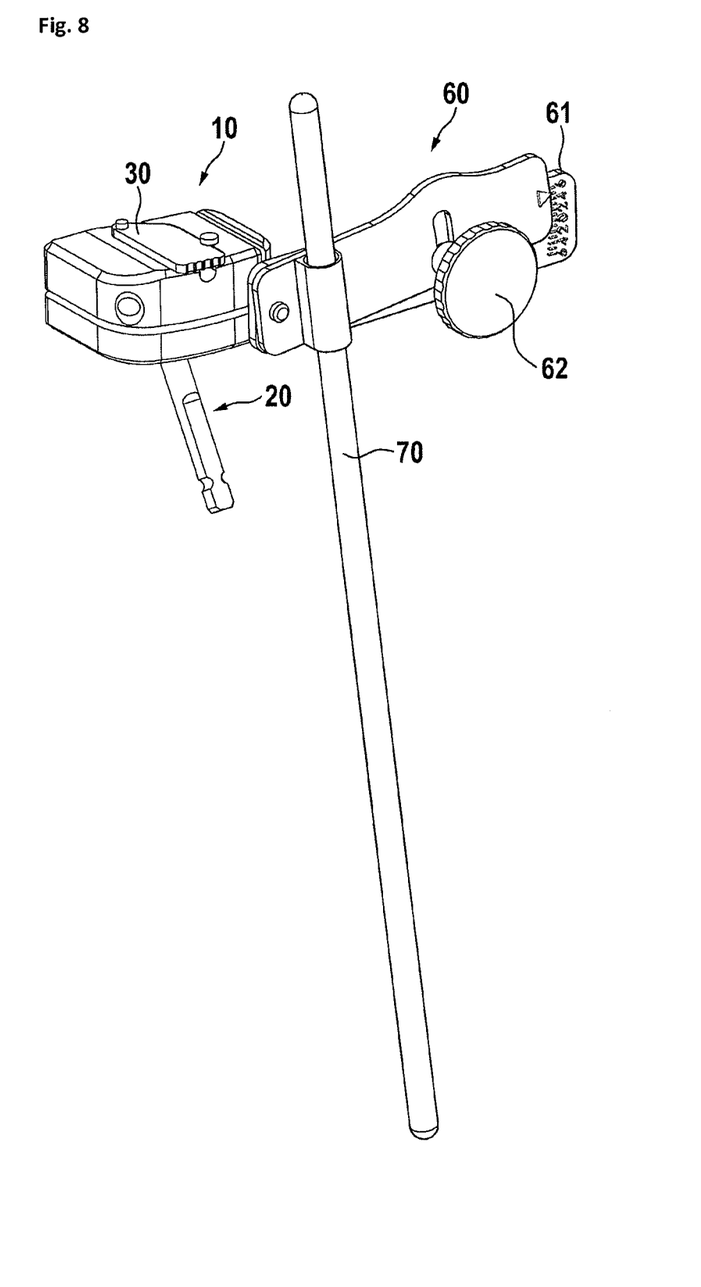
FIG. 8 shows a varus-valgus angle setting device together with an angle adapter fixed to a cutting block.

In FIG. 8, a varus-valgus angle setting device 70 together with an angle adapter 60 fixed to a cutting block 10 is shown. Here, in a preferred embodiment, the varus-valgus angle setting device 70 has a rod shape. It can be adjusted to a desired position. It may be aligned with the tibia. It may further have length and/or position indicating marks. It is connected to the cutting block by means of the angle adapter such, that a movement of the varus-valgus angle setting device results in pivoting or rotating of the cutting block around the longitudinal axis of the reference pin. The angle adapter allows to set an angle offset between the varus-valgus angle setting device and the cutting block. For indicating this offset angle, an angle offset scale 61 may be provided. Furthermore, an angle offset lock screw or any other means for locking the angle offset setting may be provided. The reference pin is not shown in this figure. The reference pin lock 30 is shown in a locked position.

Figure 9:
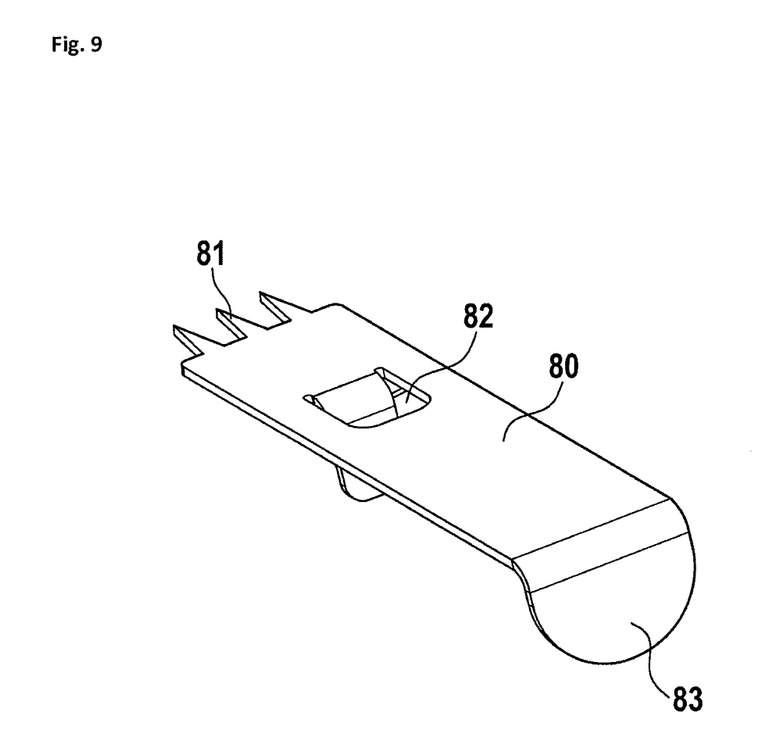
FIG. 9 shows a reference blade in detail.

FIG. 9 shows a reference blade 80 in detail. This reference blade preferably has at least one spike 81, the most preferably two or three spikes for holding the reference blade in the tibia. For simplified handling, an impact surface 83 for driving the reference blade into the bone by a hammer may be provided. Furthermore a handle 82 may be provided, which for example may be used for holding the reference blade and for pulling the reference blade out of the bone, after it has been used.

Figure 10:
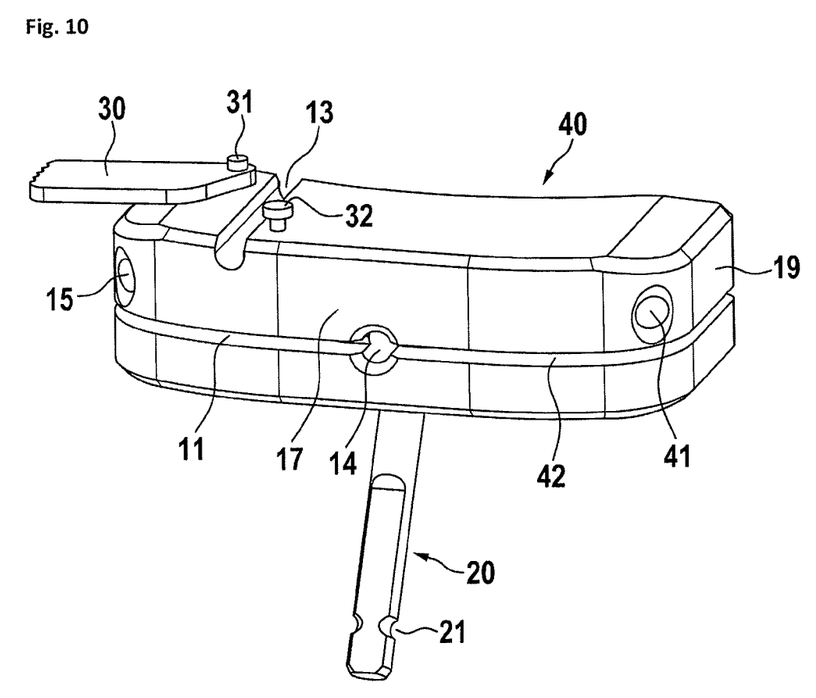
FIG. 10 shows a total prosthesis cutting block.

In FIG. 10 a total prosthesis cutting block 40 is shown. This cutting block may be used for a total tibia cut. It is similar to the cutting block shown above. The main difference is, that it has no cutting guide slot 12 for a superior-inferior cut but a second side with a second blade holding slot 42 and a third anchoring pin hole 41. The second blade holding slot may be used as an alternate to the blade holding slot for holding a reference blade 80. It may also be used as a cutting guide for a cutting blade in left-right or right-left direction.

Figure 11:
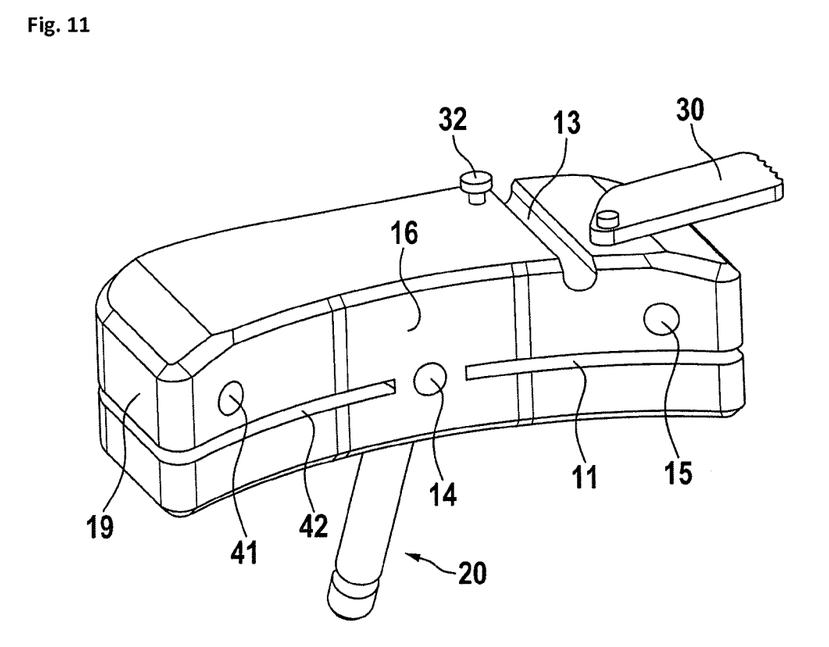
FIG. 11 shows a total prosthesis cutting block from the tibia attachment side.

FIG. 11 shows a total prosthesis cutting block from the tibia attachment side.

What is claimed is:

1. A tibia cutting block with an approximately cuboid body comprising:
   a tibia attachment side and opposing thereto a front side,
   a blade holding slot extending from a right side or a left side and penetrating the body from the front side to the tibia attachment side,
   a cutting guide slot extending from a top side and penetrating the body from the front side to the tibia attachment side,
   a first anchoring pin hole being close to an intersection of a first plane defined by the blade holding slot and a second plane defined by the a cutting guide slot, the first anchoring pin hole penetrating the body from the front side to the tibia attachment side, a second anchoring pin hole being distant from the first anchoring pin hole and penetrating the body from the front side to the tibia attachment side, and a reference pin guide groove formed in the top side and extending from the front side to the tibia attachment side.

2. A tibia cutting block with an approximately cuboid body comprising:

a tibia attachment side and opposing thereto a front side, a first blade holding slot extending from a right side or a left side and penetrating the body from the front side to the tibia attachment side, a second blade holding slot extending from a right side or a left side approximately in a same plane and opposing to the first blade holding slot, further penetrating the body from the front side to the tibia attachment side, a first anchoring pin hole being between the first blade holding slot and the second blade holding slot, the first anchoring pin hole penetrating the body from the front side to the tibia attachment side, a second anchoring pin hole being distant from the first anchoring pin hole and penetrating the body from the front side to the tibia attachment side, and a reference pin guide groove formed in a top side and extending from the front side to the tibia attachment side.

3. The tibia cutting block according to claim 1, wherein the reference pin guide extends from the front side to the tibia attachment side.

4. A tibia cutting block with an approximately cuboid body comprising:

a tibia attachment side and opposing thereto a front side, a blade holding slot extending from a right side or a left side and penetrating the body from the front side to the tibia attachment side, a cutting guide slot extending from a top side and penetrating the body from the front side to the tibia attachment side, a first anchoring pin hole being close to an intersection of a first plane defined by the blade holding slot and a second plane defined by the a cutting guide slot, the first anchoring pin hole penetrating the body from the front side to the tibia attachment side, a second anchoring pin hole being distant from the first anchoring pin hole and penetrating the body from the front side to the tibia attachment side, and a reference pin guide extending from the front side to the tibia attachment side;

wherein a reference pin lock is provided to lock a reference pin to the cutting block only allowing the cutting block to slide along a longitudinal axis of the reference pin and/or to rotate about said axis.

5. The tibia cutting block according to claim 1, wherein a width of the blade holding slot is less than the diameter of the first anchoring pin hole.

6. The tibia cutting block according to claim 1, wherein the first anchoring pin hole is not connected to the blade holding slot.

7. The tibia cutting block according to claim 1, wherein the first anchoring pin hole is not connected to the cutting guide slot.

8. The tibia cutting block according to claim 1, wherein the body comprises plastic or steel.

9. An instrument set comprising:

a tibia cutting block with an approximately cuboid body including:

a tibia attachment side and opposing thereto a front side, a blade holding slot extending from a right side or a left side and penetrating the body from the front side to the tibia attachment side, a cutting guide slot extending from a top side and penetrating the body from the front side to the tibia attachment side, a first anchoring pin hole being close to an intersection of a first plane defined by the blade holding slot and a second plane defined by the a cutting guide slot, the first anchoring pin hole penetrating the body from the front side to the tibia attachment side, a second anchoring pin hole being distant from the first anchoring pin hole and penetrating the body from the front side to the tibia attachment side, and a reference pin guide extending from the front side to the tibia attachment side;

a varus-valgus angle setting device, and an angle adapter for connecting the varus-valgus angle setting device to the tibia cutting block.

10. The instrument set of claim 9, further comprising:

a reference blade, and at least one anchoring pin.

* * * * *